(12) United States Patent
Gypser et al.

(10) Patent No.: US 6,232,339 B1
(45) Date of Patent: May 15, 2001

(54) PHENYLCARBAMATES, THEIR PREPARATION, AND COMPOSITIONS COMPRISING THEM

(75) Inventors: Andreas Gypser, Mannheim; Thomas Grote, Schifferstadt; Hubert Sauter, Mannheim; Herbert Bayer, Mannheim; Oliver Cullmann, Mannheim; Markus Gewehr, Kastellaun; Wassilios Grammenos, Ludwigshafen; Bernd Müller, Frankenthal; Arne Ptock, Ludwigshafen; Eberhard Ammermann, Heppenheim; Gisela Lorenz, Neustadt; Siegfried Strathmann, Limburgerhof; Volker Harries, Frankenthal; Franz Röhl, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/358,474

(22) Filed: Jul. 21, 1999

(30) Foreign Application Priority Data

Jul. 21, 1998 (DE) ............................... 198 32 685

(51) Int. Cl.⁷ ..................... C07C 271/28; A01N 47/18
(52) U.S. Cl. ..................... 514/485; 560/24; 560/27; 560/29; 560/30
(58) Field of Search .................. 560/27, 29, 30; 514/485

(56) References Cited

U.S. PATENT DOCUMENTS 5,650,434 * 7/1997 Ohnishi et al. .
5,824,705 10/1998 Mueller et al. ........................ 514/485
5,869,517 2/1999 Mueller et al. ........................ 514/407

FOREIGN PATENT DOCUMENTS

| 4441674 | * 5/1996 | (DE) . |
| 93/15046 | 8/1993 | (WO) . |
| 96/01256 | 1/1996 | (WO) . |
| 97/15552 | 5/1997 | (WO) . |

* cited by examiner

Primary Examiner—Gary Geist
Assistant Examiner—Leigh C Maier
(74) Attorney, Agent, or Firm—Keil & Weinkauf

(57) ABSTRACT

Phenylcarbamates of the formula I

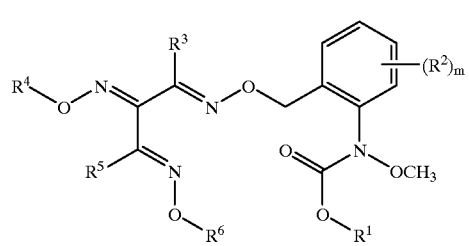

where:
$R^1$ is $C_1$–$C_4$-alkyl;
$R^2$ is cyano, nitro, trifluoromethyl, halogen, $C_1$–$C_4$-alkyl and $C_1$–$C_4$-alkoxy;
m is 0, 1 or 2, where the radicals $R^2$ may be different if m is 2;
$R^3$ is hydrogen, cyano, $C_1$–$C_4$-alkyl, $C_1$–$C_4$-haloalkyl, $C_3$–$C_6$-cycloalkyl;
$R^4$, $R^5$ and $R^6$ are each as defined in claim 1,
and salts thereof, a process and intermediates for preparing these compounds and compositions comprising them for controlling animal pests and harmful fungi are described.

10 Claims, No Drawings

PHENYLCARBAMATES, THEIR PREPARATION, AND COMPOSITIONS COMPRISING THEM

The present invention relates to phenylcarbamates of the formula I $$\text{[Structure I: phenylcarbamate with substituents } R^1, R^2, R^3, R^4, R^5, R^6, \text{OCH}_3, (R^2)_m\text{]}$$

where:

$R^1$ is $C_1$–$C_4$-alkyl;

$R^2$ is cyano, nitro, trifluoromethyl, halogen, $C_1$–$C_4$-alkyl and $C_1$–$C_4$-alkoxy;

m is 0, 1 or 2, where the radicals $R^2$ may be different if m is 2;

$R^3$ is hydrogen, cyano, $C_1$–$C_4$-alkyl, $C_1$–$C_4$-haloalkyl, $C_3$–$C_6$-cycloalkyl;

$R^4$, $R^6$ independently of one another are each hydrogen,
$C_1$–$C_{10}$-alkyl, $C_3$–$C_6$-cycloalkyl, $C_2$–$C_{10}$-alkenyl, $C_2$$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, where these radicals may be partially or fully halogenated or may carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, where the cyclic groups for their part may be partially or fully halogenated or may carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^7)$—$A_n$—$R^8$;

aryl, arylcarbonyl, arylsulfonyl, hetaryl, hetarylcarbonyl or hetarylsulfonyl, where these radicals may be partially or fully halogenated or may carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^7)$—$A_n$—$R^8$;

$R^5$ is hydrogen,
$C_1$–$C_6$-alkyl, $C_2$–$C_6$-alkenyl, $C_2$–$C_6$-alkynyl, where the hydrocarbon radicals of these groups may be partially or fully halogenated or may carry one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, where the cyclic radicals for their part may be partially or fully halogenated and/or may carry one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^7)$—$A_n$—$R^8$;

$C_3$–$C_6$-cycloalkyl, $C_3$–$C_6$-cycloalkenyl, heterocyclyl, aryl, hetaryl, where the cyclic radicals may be partially or fully halogenated or may carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy;

where

A is oxygen, sulfur or nitrogen and where the nitrogen carries hydrogen or $C_1$–$C_6$-alkyl;

n is 0 or 1;

$R^7$ is hydrogen or $C_1$–$C_6$-alkyl and $R^8$ is hydrogen or $C_1$–$C_6$-alkyl, and salts thereof.

Furthermore, the invention relates to processes and intermediates for preparing these compounds and to compositions comprising them for controlling animal pests and harmful fungi.

Phenylcarbamates having a methoximino group in the ortho position are disclosed in WO-A 93/15046. α-Phenylacrylic acid and α-phenyl-α-methoximinoacetic acid derivatives having a methoximino group in the ortho position are known from EP-A 426 460, EP-A 460 575, EP-A 472 300, EP-A 585 751, WO-A 92/13830, WO-A 92/18487, WO-A 92/18494, JP-A 05/201 946 and JP-A 05/255 012. The compounds described therein carry a $CH_2O$—N=CR'R'' group in the position ortho to the group corresponding to the carbamate substituent.

WO-A 97/15552 discloses those α-phenylacrylic acid and α-phenyl-α-methoximinoacetic acid derivatives in which the $CH_2O$—N=CR'R'' group carries cyano, alkyl, haloalkyl and cycloalkyl, and bisoxime ether groups, as substituents R' and R'', respectively.

The compounds described in the abovementioned applications are suitable for use as crop protection agents against harmful fungi and in some cases against animal pests.

It is an object of the present invention to provide novel compounds having improved activity.

We have found that this object is achieved by the phenylcarbamates I defined at the outset. Additionally, we have found processes and intermediates for their preparation, and compositions comprising them for controlling animal pests and harmful fungi, and their use to this end.

The compounds I can be obtained by various routes according to processes known per se from the literature.

In principle, when synthesizing the compounds I it is immaterial whether the carbamate group —N(OCH$_3$)—COOR$^1$ or the group

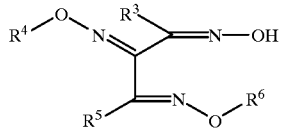

is synthesized first.

The synthesis of the carbamate group —N(OCH$_3$)—COOR$^1$ is known, for example, from WO-A 93/15046.

1. The compounds of the formula I are generally synthesized by reacting a benzyl derivative of the formula II with a hydroxyimine of the formula III.

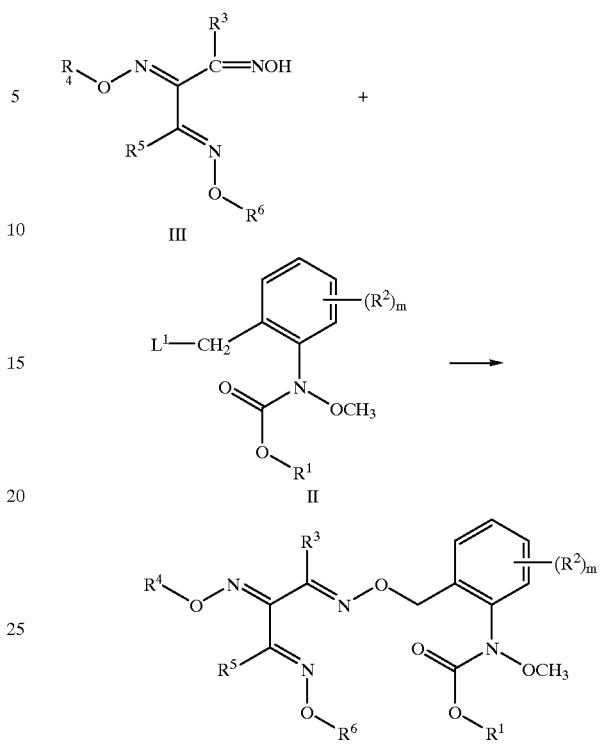

In the formula II, $L^1$ is a nucleophilically replaceable leaving group, for example halogen or a sulfonate group, preferably chlorine, bromine, iodine, mesylate, tosylate or triflate.

The reaction is carried out in a manner known per se in an inert organic solvent in the presence of a base, for example sodium hydride, potassium hydroxide, potassium carbonate and triethylamine, in accordance with the methods described in Houben-Weyl, Vol. E 14b, p. 370f. and Houben-Weyl, Vol. 10/1, p. 1189f.

The required hydroxyimines III are obtained, for example, as described in Scheme 1 by a sequence of nitrosation, alkylation and oximation reactions, from the corresponding carbonyl compounds XIV.

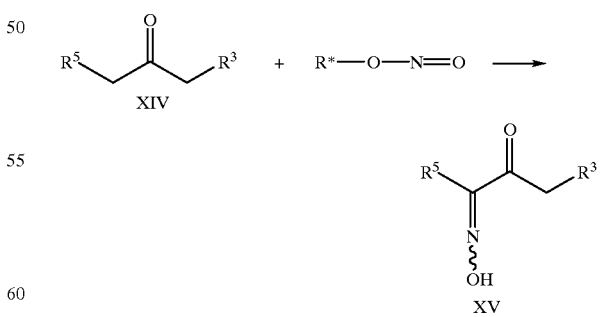

By basic or acidic catalysis, the α-ketooxime XV can be prepared from the ketone XIV using an organic nitrite, in accordance with the methods described in Houben-Weyl, Vol. 10/4, p. 17f.

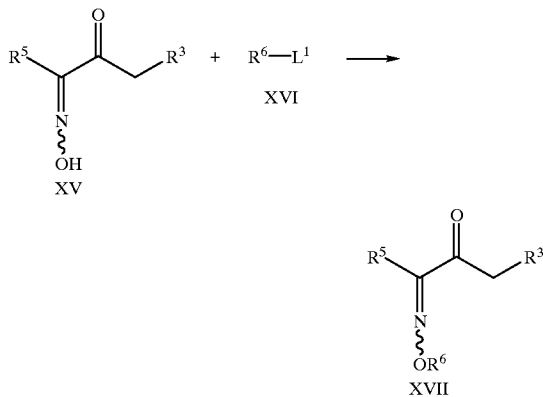

The required ketooxime ether XVII is obtained, for example, by reaction of XV with a nucleophilically substituted reagent XVI.

In the formula XVI, $L^1$ is a nucleophilically replaceable leaving group, for example halogen or a sulfonate group, preferably chlorine, bromine, iodine, mesylate, tosylate or triflate.

The reaction is carried out in a manner known per se in an inert organic solvent in the presence of a base, for example potassium carbonate, potassium hydroxide, sodium hydride, triethylamine and pyridine, in accordance with the methods described in Houben-Weyl, Vol. 14b, p. 307f., p. 370f., and p. 385f.; Houben-Weyl Vol. 10/4, p. 55f., p. 180f., and p. 217f.; Houben-Weyl Vol. E5, p. 780f.

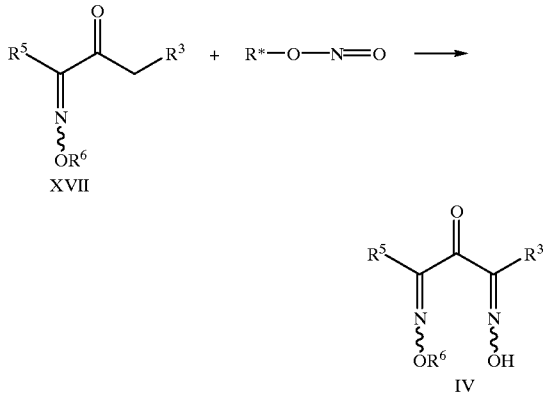

By basic or acidic catalysis, the α-ketooxime IV can be prepared from the ketone XVII, using an organic nitrite in accordance with the methods described in Houben-Weyl Vol. 10/4, p. 17f.

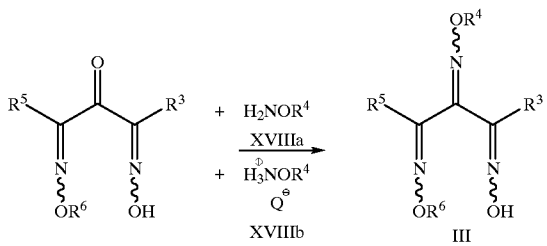

The required hydroxyimine III is obtained, for example, by reacting an appropriate α-ketooxime IV with an oxyamine XVIIIa or its salt XVIIIb. In the formula XVIIIb, $Q^\ominus$ is the anion of an acid, in particular an inorganic acid, for example a halide, such as chloride.

The reaction is carried out in a manner known per se in an inert organic solvent, in accordance with the methods described in EP-A 513 580; Houben-Weyl Vol. 10/4 p. 73f.; Houben-Weyl Vol. E14b p. 369f. and p. 385f.

1.1 Alternatively, the compounds I can also be obtained by initially reacting the benzyl derivative II with the carbonyl-hydroxyimino derivative IV to give a corresponding benzyloxyimine of the formula V, which is subsequently reacted with the hydroxylamine VIa or its salt VIb to give I.

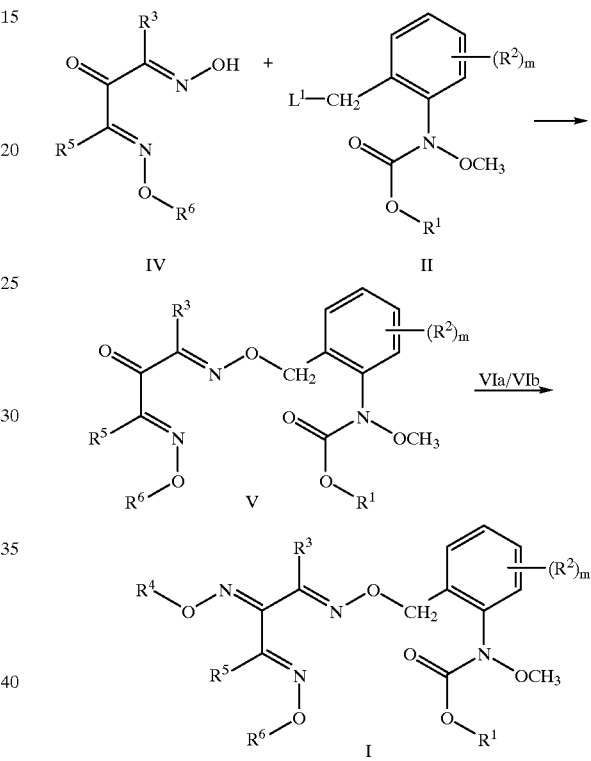

The reaction is carried out in a manner known per se in an inert organic solvent, in accordance with the methods described in Houben-Weyl, Vol. E 14b, p. 369f.; Houben-Weyl, Vol. 10/1, p. 1189f. and Houben-Weyl, Vol. 10/4, p. 73f. or EP-A 513 580.

1.2 A further route for preparing the compounds I is the reaction of the benzyl derivative II with N-hydroxyphthalimide and subsequent hydrazinolysis to give the benzylhydroxylamine IIa, followed by reaction of IIa with a carbonyl compound VII.

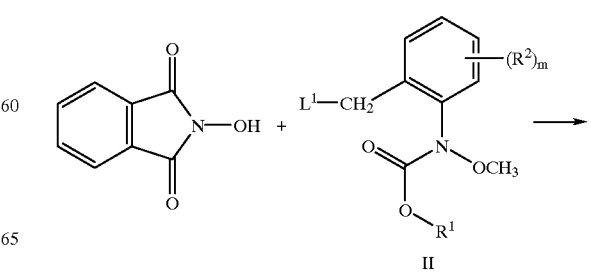

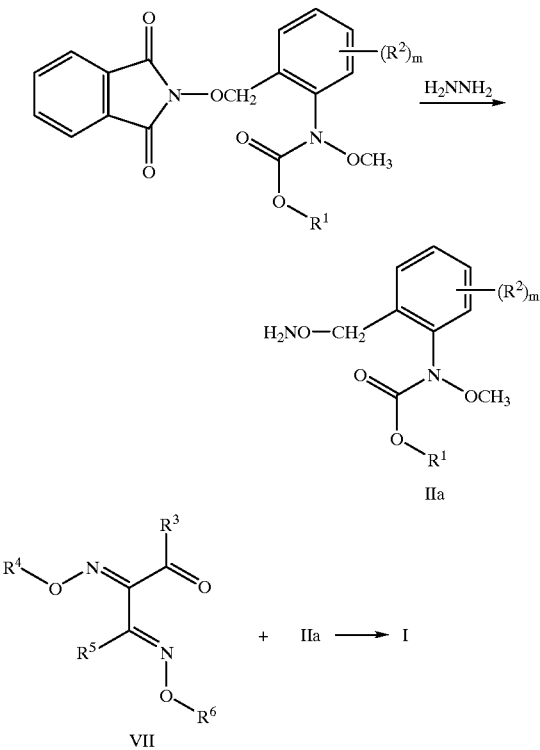

The compounds II are known (WO-A 93/15046) or can be prepared by the methods described therein.

Owing to their C=C and C=N double bonds, the compounds I can be obtained in the preparation as E/Z isomer mixtures which can be separated into the individual compounds in a customary manner for example by crystallization or chromatography.

However, if isomer mixtures are obtained in the synthesis, the separation is generally not necessarily required since in some cases the individual isomers can be converted into each other during preparation for use or upon use (for example under the influence of light, acids or bases). Corresponding conversions may also occur after the application, for example in the treatment of plants in the treated plant or in the harmful fungi or animal pest to be controlled.

With regard to the —C($R^3$)=NOCH$_2$— double bond, preference is given to the cis isomers of the compounds I with respect to their activity (configuration based on the radical $R^3$ in relation to the —OCH$_2$— group).

In the definitions of the compounds I given at the outset, collective terms were used which generally represent the following groups:

Halogen: fluorine, chlorine, bromine and iodine;

Alkyl: straight-chain or branched alkyl groups having 1 to 4, 6 or 10 carbon atoms, for example $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 6 carbon atoms, it being possible for some or all of the hydrogen atoms in these groups to be replaced by halogen atoms as mentioned above, for example $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Cycloalkyl: monocyclic alkyl groups having 3 to 6 carbon ring members, for example cyclopropyl, cyclobutyl, cyclopentyl and cyclohexyl;

Alkenyl: straight-chain or branched alkenyl groups having 2 to 6 or 10 carbon atoms and a double bond in any position, for example $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched alkynyl groups having 2 to 10 carbon atoms and a triple bond in any position, for example $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Heterocyclyl or heterocyclyloxy, heterocyclylthio and heterocyclylamino: three- to six-membered saturated or partially unsaturated mono- or polycyclic heterocycles which contain one to three heteroatoms selected from a group consisting of oxygen, nitrogen and sulfur and which are attached to the skeleton either directly or (heterocyclyloxy) via an oxygen atom or (heterocyclylthio) via a sulfur atom or (heterocyclylamino) via a nitrogen atom, such as, for example, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,3-dithian-2-yl, 1,1-dioxo-2,3,4,5-tetrahydrothien-2-yl, 2H-1,4-benzothiazin-3-yl, 1,3-dihydrooxazin-2-yl, 2H-1,4-benzoxazin-3-yl;

Aryl or aryloxy, arylthio, arylcarbonyl and arylsulfonyl: aromatic mono- or polycyclic hydrocarbon radicals which are attached to the skeleton either directly or (aryloxy) via an oxygen atom (—O—) or (arylthio) a sulfur atom (—S—), (arylcarbonyl) via a carbonyl group (—CO—) or (arylsulfonyl) via a sulfonyl group (—SO$_2$—), for example phenyl, naphthyl and phenanthrenyl or phenyloxy, naphthyloxy and phenanthrenyloxy and the corresponding carbonyl and sulfonyl radicals;

Hetaryl or hetaryloxy, hetarylthio, hetarylcarbonyl and hetarylsulfonyl: aromatic mono- or polycyclic radicals which, in addition to carbon ring members, may additionally contain one to four nitrogen atoms or one to three nitrogen atoms and one oxygen or one sulfur atom or one oxygen or one sulfur atom and which are attached to the skeleton either directly or (hetaryloxy) via an oxygen atom (—O—) or (hetarylthio) a sulfur atom (—S—), (hetarylcarbonyl) via a carbonyl group (—CO—) or (hetarylsulfonyl) via a sulfonyl group (—SO$_2$—), for example 5-membered hetaryl, containing one to three nitrogen atoms: 5-membered hetaryl groups which may, in addition to carbon atoms, contain one to three nitrogen atoms as ring members, for example 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl, containing one to four nitrogen atoms or one to three nitrogen atoms and one sulfur or oxygen atom or one oxygen or one sulfur atom: 5-membered hetaryl groups which may, in addition to carbon atoms, contain one to four nitrogen atoms or one to three nitrogen atoms and one sulfur or oxygen atom or one oxygen or sulfur atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl, containing one to three nitrogen atoms or one nitrogen atom and/or one oxygen or sulfur atom: 5-membered hetaryl groups which may, in addition to carbon atoms, contain one to four nitrogen atoms or one to three nitrogen atoms and one sulfur or oxygen atom or one oxygen or one sulfur atom as ring members, and in which two adjacent carbon ring members or one nitrogen and one adjacent carbon ring member may be bridged by a buta-1,3-diene-1,4-diyl group;

5-membered hetaryl which is attached via nitrogen and contains one to four nitrogen atoms, or benzo-fused 5-membered hetaryl which is attached via nitrogen and contains one to three nitrogen atoms: 5-membered hetaryl groups which may, in addition to carbon atoms, contain one to four nitrogen atoms or one to three nitrogen atoms as ring members and in which two adjacent carbon ring members or one nitrogen and one adjacent carbon ring member may be bridged by a buta-1,3-diene-1,4-diyl group, where these rings are attached to the skeleton via one of the nitrogen ring members;

6-membered hetaryl, containing one to three or one to four nitrogen atoms: 6-membered hetaryl groups which may, in addition to carbon atoms, contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl, containing one to four nitrogen atoms: 6-membered hetaryl groups in which two adjacent carbon ring members may be bridged by a buta-1,3-diene-1,4-diyl group, for example quinoline, isoquinoline, quinazoline and quinoxaline, or the corresponding oxy, thio, carbonyl or sulfonyl groups.

Hetarylamino: aromatic mono- or polycyclic radicals which may, in addition to carbon ring members, additionally contain one to four nitrogen atoms or one to three nitrogen atoms and one oxygen or one sulfur atom and which are attached to the skeleton via a nitrogen atom.

The term "partially or fully halogenated" is meant to express that the hydrogen atoms in the groups which are characterized in such a way may be partially or fully replaced by identical or different halogen atoms as mentioned above.

With regard to their biological activity, preference is given to compounds of the formula I in which m is 0.

Likewise, preference is given to compounds of the formula I in which $R^1$ is methyl.

In addition, preference is given to compounds I in which $R^3$ is hydrogen, cyano, cyclopropyl, methyl, ethyl, 1-methylethyl or $CF_3$.

Moreover, preference is given to compounds I in which $R^3$ is methyl.

In addition, preference is given to compounds I in which $R^3$ is cyano.

Furthermore, preference is given to compounds I in which $R^3$ is cyclopropyl.

Furthermore, preference is given to compounds I in which $R^3$ is $CF_3$.

Furthermore, preference is given to compounds I in which $R^5$ is hydrogen, cyclopropyl, methyl, ethyl, isopropyl, unsubstituted or substituted aryl or hetaryl.

Moreover, preference is given to compounds I in which $R^5$ is methyl.

Furthermore, preference is given to compounds I in which $R^5$ is ethyl.

Moreover, preference is given to compounds I in which $R^5$ is isopropyl.

Moreover, preference is given to compounds I in which $R^5$ is cyclopropyl.

Moreover, preference is given to compounds I in which $r^5$ is $CF_3$

Furthermore, preference is given to compounds I in which $R^5$ is unsubstituted or substituted aryl or hetaryl.

Furthermore, preference is given to compounds I in which $R^5$ is unsubstituted or substituted pyridyl, pyrimidyl, pyrazinyl, pyridazinyl or triazinyl.

Furthermore, preference is given to compounds I in which $R^5$ is unsubstituted or substituted furyl, thienyl or pyrrolyl.

Furthermore, preference is given to compounds I in which $R^5$ is unsubstituted or substituted oxazolyl, thiazolyl, isoxazolyl, isothiazolyl, pyrazolyl or imidazolyl.

Furthermore, preference is given to compounds I in which $R^5$ is unsubstituted or substituted oxadiazolyl, thiadiazolyl or triazolyl.

Moreover, preference is given to compounds I in which $R^5$ is phenyl which is unsubstituted or carries one or two of the following groups: nitro, cyano, hydroxyl, amino, aminocarbonyl, aminothiocarbonyl, halogen, $C_1-C_4$-alkyl, $C_1-C_4$-haloalkyl, $C_1-C_4$-alkoxy, $C_1-C_4$-haloalkoxy, $C_1-C_4$-alkylamino, di-$C_1-C_4$-alkylamino, $C_1-C_4$-alkylsulfonyl, $C_1-C_4$-alkoxycarbonyl, $C_1-C_4$-alkylaminocarbonyl or di-$C_1-C_4$-alkylaminocarbonyl.

Moreover, preference is given to compounds I in which $R^4$ is hydrogen, $C_1-C_6$-alkyl, $C_2-C_6$-alkenyl, $C_2-C_6$-alkynyl, allyl, arylalkyl, hetarylalkyl, aryloxyalkyl, hetaryloxyalkyl, aryl or hetaryl.

Furthermore, preference is given to compounds I in which $R^4$ is $C_1-C_6$-alkyl.

Moreover, preference is given to compounds I in which $R^4$ is methyl, ethyl, 2-propenyl or 2-propynyl.

Furthermore, preference is given to compounds of the formula I in which $R^6$ is $C_1-C_6$-alkyl, $C_2-C_6$-alkenyl, $C_2-C_6$-alkynyl, arylalkyl, hetarylalkyl, aryloxyalkyl or hetaryloxyalkyl.

Moreover, preference is given to compounds I in which $R^6$ is methyl, ethyl or propargyl.

Furthermore, preference is given to those compounds I in which $R^6$ is arylalkyl or hetarylalkyl.

Moreover, preference is given to those compounds I in which $R^6$ is aryloxyalkyl or hetaryloxyalkyl.

Furthermore, preference is given to compounds of the formula I in which the substituents are selected from a combination of the preferred substituents described above.

With respect to their use, particular preference is given to the compounds of the formula I.1 compiled in the tables below:

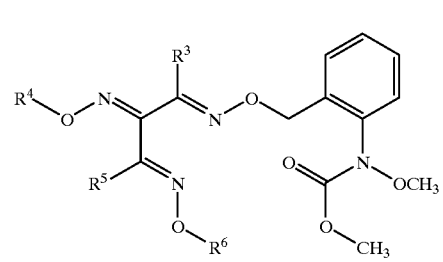

I.1

Table 1:
Compounds of the formula I.1, in which $R^3$=methyl, $R^4$=methyl and $R^5$=hydrogen and the substituent $R^6$ corresponds for each compound to one line of Table A.

Table 2:
Compounds of the formula I.1, in which $R^3$=methyl, $R^4$=methyl and $R^5$=methyl and the substituent $R^6$ corresponds for each compound to one line of Table A.

Table 3:
Compounds of the formula I.1, in which $R^3$=methyl, $R^4$=methyl and $R^5$=ethyl and the substituent $R^6$ corresponds for each compound to one line of Table A.

Table 4:
Compounds of the formula I.1, in which $R^3$=methyl, $R^4$=methyl and $R^5$=n-propyl and the substituent $R^6$ corresponds for each compound to one line of Table A.

Table 5:
Compounds of the formula I.1, in which $R^3$=methyl, $R^4$=methyl and $R^5$=i-propyl and the substituent $R^6$ corresponds for each compound to one line of Table A.

Table 6:
Compounds of the formula I.1, in which $R^3$=methyl, $R^4$=methyl and $R^5$=cyclopropyl and the substituent $R^6$ corresponds for each compound to one line of Table A.

Table 7:
Compounds of the formula I.1, in which $R^3$=methyl, $R^4$=methyl and $R^5$=cyano and the substituent $R^6$ corresponds for each compound to one line of Table A.

Table 8:
Compounds of the formula I.1, in which $R^3$=methyl, $R^4$=ethyl and $R^5$=hydrogen and the substituent $R^6$ corresponds for each compound to one line of Table A.

Table 9:
Compounds of the formula I.1, in which $R^3$=methyl, $R^4$=ethyl and $R^5$=methyl and the substituent $R^6$ corresponds for each compound to one line of Table A.

Table 10:
Compounds of the formula 1.1, in which $R^3$=methyl, $R^4$=ethyl and $R^5$=ethyl and the substituent $R^6$ corresponds for each compound to one line of Table A.

Table 11:
Compounds of the formula I.1, in which $R^3$=methyl, $R^4$=ethyl and $R^5$=n-propyl and the substituent $R^6$ corresponds for each compound to one line of Table A.

Table 12:
Compounds of the formula I.1, in which $R^3$=methyl, $R^4$=ethyl and $R^5$=i-propyl and the substituent $R^6$ corresponds for each compound to one line of Table A.

Table 13:
Compounds of the formula I.1, in which $R^3$=methyl, $R^4$=ethyl and $R^5$=cyclopropyl and the substituent $R^6$ corresponds for each compound to one line of Table A.

Table 14:
Compounds of the formula I.1, in which $R^3$=methyl, $R^4$=ethyl and $R^5$=cyano and the substituent $R^6$ corresponds for each compound to one line of Table A.

Table 15:
Compounds of the formula I.1, in which $R^3$=methyl, $R^4$=propargyl and $R^5$=hydrogen and the substituent $R^6$ corresponds for each compound to one line of Table A.

Table 16:
Compounds of the formula I.1, in which $R^3$=methyl, $R^4$=propargyl and $R^5$=methyl and the substituent $R^6$ corresponds for each compound to one line of Table A.

Table 17:
Compounds of the formula I.1, in which $R^3$=methyl, $R^4$=propargyl and $R^5$=ethyl and the substituent $R^6$ corresponds for each compound to one line of Table A.

Table 18:
Compounds of the formula I.1, in which $R^3$=methyl, $R^4$=propargyl and $R^5$=n-propyl and the substituent $R^6$ corresponds for each compound to one line of Table A.

Table 19:
Compounds of the formula I.1, in which $R^3$=methyl, $R^4$=propargyl and $R^5$=i-propyl and the substituent $R^6$ corresponds for each compound to one line of Table A.

Table 20:
Compounds of the formula I.1, in which $R^3$=methyl, $R^4$=propargyl and $R^5$=cyclopropyl and the substituent $R^6$ corresponds for each compound to one line of Table A.

Table 21:
Compounds of the formula I.1, in which $R^3$=methyl, $R^4$=propargyl and $R^5$=cyano and the substituent $R^6$ corresponds for each compound to one line of Table A.

Table 22:
Compounds of the formula I.1, in which $R^3$=trifluoromethyl, $R^4$=methyl and $R^5$=methyl and the substituent $R^6$ corresponds for each compound to one line of Table A.

Table 23:
Compounds of the formula I.1, in which $R^3$=trifluoromethyl, $R^4$=ethyl and $R^5$=methyl and the substituent $R^6$ corresponds for each compound to one line of Table A.

Table 24:
Compounds of the formula I.1, in which $R^3$=trifluoromethyl, $R^4$=propargyl and $R^5$=methyl and the substituent $R^6$ corresponds for each compound to one line of Table A.

Table 25:
Compounds of the formula I.1, in which $R^3$=cyclopropyl, $R^4$=methyl and $R^5$=methyl and the substituent $R^6$ corresponds for each compound to one line of Table A.

Table 26:
Compounds of the formula I.1, in which $R^3$=cyclopropyl, $R^4$=ethyl and $R^5$=methyl and the substituent $R^6$ corresponds for each compound to one line of Table A.

Table 27:
Compounds of the formula I.1, in which $R^3$=cyclopropyl, $R^4$=propargyl and $R^5$=methyl and the substituent $R^6$ corresponds for each compound to one line of Table A.

Table 28:
Compounds of the formula I.1, in which $R^3$=cyano, $R^4$=methyl and $R^5$=methyl and the substituent $R^6$ corresponds for each compound to one line of Table A.

Table 29:
Compounds of the formula I.1, in which $R^3$=cyano, $R^4$=ethyl and $R^5$=methyl and the substituent $R^6$ corresponds for each compound to one line of Table A.

Table 30:
Compounds of the formula I.1, in which $R^3$=cyano, $R^4$=propargyl and $R^5$=methyl and the substituent $R^6$ corresponds for each compound to one line of Table A.

TABLE A

| No. | $R^6$ |
|---|---|
| 1 | H |
| 2 | $CH_3$ |
| 3 | $CH_2CH_3$ |
| 4 | $CH_2CH_2CH_3$ |
| 5 | $CH(CH_3)_2$ |
| 6 | cyclopropyl |
| 7 | $(CH_2)_3CH_3$ |
| 8 | $CH(CH_3)CH_2CH_3$ |
| 9 | $CH_2CH(CH_3)_2$ |
| 10 | $C(CH_3)_3$ |
| 11 | cyclobutyl |
| 12 | $(CH_2)_4CH_3$ |
| 13 | $CH(CH_3)(CH_2)_2CH_3$ |
| 14 | $CH_2CH(CH_3)CH_2CH_3$ |
| 15 | $(CH_2)_2CH(CH_3)_2$ |
| 16 | $CH_2C(CH_3)_3$ |
| 17 | $CH(CH_2CH_3)_2$ |
| 18 | $C(CH_3)_2CH_2CH_3$ |
| 19 | $CH(CH_3)CH(CH_3)_2$ |
| 20 | cyclopentyl |
| 21 | $(CH_2)_5CH_3$ |
| 22 | $CH(CH_3)(CH_2)_3CH_3$ |
| 23 | $CH(CH_2CH_3)(CH_2)_2CH_3$ |
| 24 | $CH_2CH(CH_3)(CH_2)_2CH_3$ |
| 25 | $(CH_2)_2CH(CH_3)CH_2CH_3$ |
| 26 | $(CH_2)_3CH(CH_3)_2$ |
| 27 | $(CH_2)_2C(CH_3)_3$ |
| 28 | $CH_2CH(CH_2CH_3)_2$ |
| 29 | $CH(CH_3)CH(CH_3)CH_2CH_3$ |
| 30 | $CH(CH_3)CH_2CH(CH_3)_2$ |
| 31 | $CH_2CH(CH_3)CH(CH_3)_2$ |
| 32 | $CH(CH_3)C(CH_3)_3$ |
| 33 | $CH(CH_2CH_3)CH(CH_3)_2$ |
| 34 | $C(CH_3)_2CH_2CH_2CH_3$ |
| 35 | $CH_2C(CH_3)_2CH_2CH_3$ |
| 36 | $C(CH_3)_2CH(CH_3)_2$ |
| 37 | cyclohexyl |
| 38 | $CH_2CN$ |
| 39 | $(CH_2)_2CN$ |
| 40 | $(CH_2)_3CN$ |
| 41 | $(CH_2)_4CN$ |
| 42 | $(CH_2)_2OCH_3$ |
| 43 | $(CH_2)_3OCH_3$ |
| 44 | $(CH_2)_4OCH_3$ |
| 45 | $(CH_2)_2OCH_2CH_3$ |
| 46 | $(CH_2)_3OCH_2CH_3$ |
| 47 | $(CH_2)_4OCH_2CH_3$ |
| 48 | $(CH_2)_2O(CH_2)_2CH_3$ |
| 49 | $(CH_2)_3O(CH_2)_2CH_3$ |
| 50 | $(CH_2)_4O(CH_2)_2CH_3$ |
| 51 | $(CH_2)_2OCH(CH_3)_2$ |
| 52 | $(CH_2)_3OCH(CH_3)_2$ |
| 53 | $(CH_2)_4OCH(CH_3)_2$ |
| 54 | $(CH_2)_2OC(CH_3)_3$ |
| 55 | $(CH_2)_3OC(CH_3)_3$ |
| 56 | $(CH_2)_4OC(CH_3)_3$ |
| 57 | $(CH_2)_2OCF_3$ |
| 58 | $(CH_2)_3OCF_3$ |
| 59 | $(CH_2)_4OCF_3$ |
| 60 | $(CH_2)_2SCH_3$ |
| 61 | $CH_3(CH_2)_3SCH_3$ |
| 62 | $(CH_2)_4SCH_3$ |
| 63 | $CH_2$-cyclopropyl |
| 64 | $(CH_2)_2$-cyclopropyl |
| 65 | $(CH_2)3$-cyclopropyl |
| 66 | $(CH_2)_4$-cyclopropyl |
| 67 | $CH_2$-cyclopentyl |

TABLE A-continued

| No. | R⁶ |
|---|---|
| 68 | (CH₂)₂-cyclopentyl |
| 69 | (CH₂)₃-cyclopentyl |
| 70 | (CH₂)₄-cyclopentyl |
| 71 | CH₂-cyclohexyl |
| 72 | (CH₂)₂-cyclohexyl |
| 73 | (CH₂)₃-cyclohexyl |
| 74 | (CH₂)₄-cyclohexyl |
| 75 | CHF₂ |
| 76 | CF₃ |
| 77 | CH₂CHF₂ |
| 78 | CH₂CF₃ |
| 79 | CHFCHF₂ |
| 80 | CH₂CH₂F |
| 81 | CHFCH₃ |
| 82 | CHFCF₃ |
| 83 | CF₂CHF₂ |
| 84 | CF₂CHFCF₃ |
| 85 | CH₂CCl₃ |
| 86 | CF₂CHCl₂ |
| 87 | CF₂CHFCl |
| 88 | CF₂CHFBr |
| 89 | CH(CF₃)₂ |
| 90 | CH(CF₃)CH₃ |
| 91 | CH₂CH₂CF₃ |
| 92 | CH₂CHFCH₃ |
| 93 | CH₂CF₂CF₃ |
| 94 | CH₂CH₂CH₂F |
| 95 | CH₂CF₂CF₂CF₃ |
| 96 | CH₂CH₂CHFCH₃ |
| 97 | CH₂CH₂CH₂CH₂F |
| 98 | CH₂CH₂Cl |
| 99 | CH₂CHClCH₃ |
| 100 | CH₂CH₂CH₂Cl |
| 101 | CH₂CH₂CHClCH₃ |
| 102 | CH₂CH₂CH₂CH₂Cl |
| 103 | CH₂CH₂Br |
| 104 | CH₂CHBrCH₃ |
| 105 | CH₂CH₂CH₂Br |
| 106 | CH₂CH₂CHBrCH₃ |
| 107 | CH₂CH₂CH₂CH₂Br |
| 108 | CH₂—C₆H₅ |
| 109 | CH(CH₃)CN |
| 110 | CH(CH₃)CH₂CN |
| 111 | CH₂CH(CH₃)CN |
| 112 | CH(CH₃)CH(CH₃)CN |
| 113 | CH(CH₃)(CH₂)₂CN |
| 114 | CH₂CH(CH₃)CH₂CN |
| 115 | (CH₂)₂CH(CH₃)CN |
| 116 | CH(CH₃)CH(CH₃)CH₂CN |
| 117 | CH(CH₃)CH₂CH(CH₃)CN |
| 118 | CH₂CH(CH₃)CH(CH₃)CN |
| 119 | CH(CH₃)CH(CH₃)CH(CH₃)CN |
| 120 | CH(CH₃)(CH₂)₃CN |
| 121 | CH(CH₃)CH₂OH |
| 122 | CH₂CH(CH₃)OH |
| 123 | CH(CH₃)CH(CH₃)OH |
| 124 | CH(CH₃)(CH₂)₂OH |
| 125 | CH₂CH(CH₃)CH₂OH |
| 126 | (CH₂)₂CH(CH₃)OH |
| 127 | CH(CH₃)CH(CH₃)CH₂OH |
| 128 | CH(CH₃)CH₂CH(CH₃)OH |
| 129 | CH₂CH(CH₃)CH(CH₃)OH |
| 130 | CH(CH₃)CH(CH₃)CH(CH₃)OH |
| 131 | CH(CH₃)(CH₂)₃OH |
| 132 | CH(CH₃)CH₂OCH₃ |
| 133 | CH₂CH(CH₃)OCH₃ |
| 134 | CH(CH₃)CH(CH₃)OCH₃ |
| 135 | CH(CH₃)(CH₂)₂OCH₃ |
| 136 | CH₂CH(CH₃)CH₂OCH₃ |
| 137 | (CH₂)₂CH(CH₃)OCH₃ |
| 138 | CH(CH₃)CH(CH₃)CH₂OCH₃ |
| 139 | CH(CH₃)CH₂CH(CH₃)OCH₃ |
| 140 | CH₂CH(CH₃)CH(CH₃)OCH₃ |
| 141 | CH(CH₃)CH(CH₃)CH(CH₃)OCH₃ |
| 142 | CH(CH₃)(CH₂)₃OCH₃ |
| 143 | CH(CH₃)CH₂OCH₂CH₃ |
| 144 | CH₂CH(CH₃)OCH₂CH₃ |
| 145 | CH(CH₃)CH(CH₃)OCH₂CH₃ |
| 146 | CH(CH₃)(CH₂)₂OCH₂CH₃ |
| 147 | CH₂CH(CH₃)CH₂OCH₂CH₃ |
| 148 | (CH₂)₂CH(CH₃)OCH₂CH₃ |
| 149 | CH(CH₃)CH(CH₃)CH₂OCH₂CH₃ |
| 150 | CH(CH₃)CH₂CH(CH₃)OCH₂CH₃ |
| 151 | CH₂CH(CH₃)CH(CH₃)OCH₂CH₃ |
| 152 | CH(CH₃)CH(CH₃)CH(CH₃)OCH₂CH₃ |
| 153 | CH(CH₃)₃OCH₂CH₃ |
| 154 | CH(CH₃)CH₂O(CH₂)₂CH₃ |
| 155 | CH₂CH(CH₃)O(CH₂)₂CH₃ |
| 156 | CH(CH₃)CH(CH₃)O(CH₂)₂CH₃ |
| 157 | CH(CH₃)(CH₂)₂O(CH₂)₂CH₃ |
| 158 | CH₂CH(CH₃)CH₂O(CH₂)₂CH₃ |
| 159 | (CH₂)₂CH(CH₃)O(CH₂)₂CH₃ |
| 160 | CH(CH₃)CH(CH₃)CH₂O(CH₂)₂CH₃ |
| 161 | CH(CH₃)CH₂CH(CH₃)O(CH₂)₂CH₃ |
| 162 | CH₂CH(CH₃)CH(CH₃)O(CH₂)₂CH₃ |
| 163 | CH(CH₃)CH(CH₃)CH(CH₃)O(CH₂)₂CH₃ |
| 164 | CH(CH₃)(CH₂)₃O(CH₂)₂CH₃ |
| 165 | CH(CH₃)CH₂OCH(CH₃)₂ |
| 166 | CH₂CH(CH₃)OCH(CH₃)₂ |
| 167 | CH(CH₃)CH(CH₃)OCH(CH₃)₂ |
| 168 | CH(CH₃)(CH₂)₂OCH(CH₃)₂ |
| 169 | CH₂CH(CH₃)CH₂OCH(CH₃)₂ |
| 170 | (CH₂)₂CH(CH₃)OCH(CH₃)₂ |
| 171 | CH(CH₃)CH(CH₃)CH₂OCH(CH₃)₂ |
| 172 | CH(CH₃)CH₂CH(CH₃)OCH(CH₃)₂ |
| 173 | CH₂CH(CH₃)CH(CH₃)OCH(CH₃)₂ |
| 174 | CH(CH₃)CH(CH₃)CH(CH₃)OCH(CH₃)₂ |
| 175 | CH(CH₃)(CH₂)₃OCH(CH₃)₂ |
| 176 | CH(CH₃)CH₂OC(CH₃)₃ |
| 177 | CH₂CH(CH₃)OC(CH₃)₃ |
| 178 | CH(CH₃)CH(CH₃)OC(CH₃)₃ |
| 179 | CH(CH₃)(CH₂)₂OC(CH₃)₃ |
| 180 | CH₂CH(CH₃)CH₂OC(CH₃)₃ |
| 181 | (CH₂)₂CH(CH₃)OC(CH₃)₃ |
| 182 | CH(CH₃)CH(CH₃)CH₂OC(CH₃)₃ |
| 183 | CH(CH₃)CH₂CH(CH₃)OC(CH₃)₃ |
| 184 | CH₂CH(CH₃)CH(CH₃)OC(CH₃)₃ |
| 185 | CH(CH₃)CH(CH₃)CH(CH₃)OC(CH₃)₃ |
| 186 | CH(CH₃)(CH₂)₃OC(CH₃)₃ |
| 187 | CH(CH₃)CH₂OCF₃ |
| 188 | CH₂CH(CH₃)OCF₃ |
| 189 | CH(CH₃)CH(CH₃)OCF₃ |
| 190 | CH(CH₃)(CH₂)₂OCF₃ |
| 191 | CH₂CH(CH₃)CH₂OCF₃ |
| 192 | (CH₂)₂CH(CH₃)OCF₃ |
| 193 | CH(CH₃)CH(CH₃)CH₂OCF₃ |
| 194 | CH(CH₃)CH₂CH(CH₃)OCF₃ |
| 195 | CH₂CH(CH₃)CH(CH₃)OCF₃ |
| 196 | CH(CH₃)CH(CH₃)CH(CH₃)OCF₃ |
| 197 | CH(CH₃)(CH₂)₃OCF₃ |
| 198 | CH(CH₃)CH₂SCH₃ |
| 199 | CH₂CH(CH₃)SCH₃ |
| 200 | CH(CH₃)CH(CH₃)SCH₃ |
| 201 | CH(CH₃)(CH₂)₂SCH₃ |
| 202 | CH₂CH(CH₃)CH₂SCH₃ |
| 203 | (CH₂)₂CH(CH₃)SCH₃ |
| 204 | CH(CH₃)CH(CH₃)CH₂SCH₃ |
| 205 | CH(CH₃)CH₂CH(CH₃)SCH₃ |
| 206 | CH₂CH(CH₃)CH(CH₃)SCH₃ |
| 207 | CH(CH₃)CH(CH₃)CH(CH₃)SCH₃ |
| 208 | CH(CH₃)(CH₂)₃SCH₃ |
| 209 | CH(CH₃)CH₂SOCH₃ |
| 210 | CH₂CH(CH₃)SOCH₃ |
| 211 | CH(CH₃)-cyclopropyl |
| 212 | CH(CH₃)CH₂-cyclopropyl |
| 213 | CH₂CH(CH₃)-cyclopropyl |
| 214 | CH(CH₃)CH(CH₃)-cyclopropyl |
| 215 | CH(CH₃)(CH₂)₂-cyclopropyl |
| 216 | CH₂CH(CH₃)CH₂-cyclopropyl |
| 217 | (CH₂)₂CH(CH₃)-cyclopropyl |
| 218 | CH(CH₃)CH(CH₃)CH₂-cyclopropyl |
| 219 | CH(CH₃)CH₂CH(CH₃)-cyclopropyl |
| 220 | CH₂CH(CH₃)CH(CH₃)-cyclopropyl |
| 221 | CH(CH₃)CH(CH₃)CH(CH₃)-cyclopropyl |

TABLE A-continued

| No. | R$^6$ |
|---|---|
| 222 | CH(CH$_3$)(CH$_2$)3-cyclopropyl |
| 223 | CH(CH$_3$)-cyclopentyl |
| 224 | CH(CH$_3$)CH$_2$-cyclopentyl |
| 225 | CH$_2$CH(CH$_3$)-cyclopentyl |
| 226 | CH(CH$_3$)CH(CH$_3$)-cyclopentyl |
| 227 | CH(CH$_3$)(CH$_2$)$_2$-cyclopentyl |
| 228 | CH$_2$CH(CH$_3$)CH$_2$-cyclopentyl |
| 229 | (CH$_2$)$_2$CH(CH$_3$)-cyclopentyl |
| 230 | CH(CH$_3$)CH(CH$_3$)CH$_2$-cyclopentyl |
| 231 | CH(CH$_3$)CH$_2$CH(CH$_3$)-cyclopentyl |
| 232 | CH$_2$CH(CH$_3$)CH(CH$_3$)-cyclopentyl |
| 233 | CH(CH$_3$)CH(CH$_3$)CH(CH$_3$)-cyclopentyl |
| 234 | CH(CH$_3$)(CH$_2$)$_3$-cyclopentyl |
| 235 | CH(CH$_3$)-cyclohexyl |
| 236 | CH(CH$_3$)CH$_2$-cyclohexyl |
| 237 | CH$_2$CH(CH$_3$)-cyclohexyl |
| 238 | CH(CH$_3$)CH(CH$_3$)-cyclohexyl |
| 239 | CH(CH$_3$)(CH$_2$)$_2$-cyclohexyl |
| 240 | CH$_2$CH(CH$_3$)CH$_2$-cyclohexyl |
| 241 | (CH$_2$)$_2$CH(CH$_3$)-cyclohexyl |
| 242 | CH(CH$_3$)CH(CH$_3$)CH$_2$-cyclohexyl |
| 243 | CH(CH$_3$)CH$_2$CH(CH$_3$)-cyclohexyl |
| 244 | CH$_2$CH(CH$_3$)CH(CH$_3$)-cyclohexyl |
| 245 | CH(CH$_3$)CH(CH$_3$)CH(CH$_3$)-cyclohexyl |
| 246 | CH(CH$_3$)(CH$_2$)$_3$-cyclohexyl |
| 247 | CH(CH$_3$)CHF$_2$ |
| 248 | CF(CH$_3$)CHF$_2$ |
| 249 | CH(CH$_3$)CH$_2$F |
| 250 | CF(CH$_3$)CH$_3$ |
| 251 | CF(CH$_3$)CF$_3$ |
| 252 | CH(CH$_3$)CCl$_3$ |
| 253 | CH(CH$_3$)CH$_2$CF$_3$ |
| 254 | CH$_2$CH(CH$_3$)CF$_3$ |
| 255 | CH(CH$_3$)CH(CH$_3$)CF$_3$ |
| 256 | CH(CH$_3$)CF$_2$CF$_3$ |
| 257 | CH(CH$_3$)-phenyl |
| 258 | CH(CH$_3$)CH$_2$-phenyl |
| 259 | CH$_2$CH(CH$_3$)-phenyl |
| 260 | CH(CH$_3$)CH(CH$_3$)-phenyl |
| 261 | CH(CH$_3$)(CH$_2$)$_2$-phenyl |
| 262 | CH$_2$CH(CH$_3$)CH$_2$-phenyl |
| 263 | (CH$_2$)$_2$CH(CH$_3$)-phenyl |
| 264 | CH(CH$_3$)CH(CH$_3$)CH$_2$-phenyl |
| 265 | CH(CH$_3$)CH$_2$CH(CH$_3$)-phenyl |
| 266 | CH$_2$CH(CH$_3$)CH(CH$_3$)-phenyl |
| 267 | CH(CH$_3$)CH(CH$_3$)CH(CH$_3$)-phenyl |
| 268 | CH(CH$_3$)(CH$_2$)$_3$-phenyl |
| 269 | 2-CH$_3$—C$_6$H$_4$—CH$_2$ |
| 270 | 3-CH$_3$—C$_6$H$_4$—CH$_2$ |
| 271 | 4-CH$_3$—C$_6$H$_4$—CH$_2$ |
| 272 | 2,3-(CH$_3$)$_2$-C$_6$H$_3$—CH$_2$ |
| 273 | 2,4-(CH$_3$)$_2$-C$_6$H$_3$—CH$_2$ |
| 274 | 2,5-(CH$_3$)$_2$-C$_6$H$_3$—CH$_2$ |
| 275 | 2,6-(CH$_3$)$_2$-C$_6$H$_3$—CH$_2$ |
| 276 | 3,4-(CH$_3$)$_2$-C$_6$H$_3$—CH$_2$ |
| 277 | 3,5-(CH$_3$)$_2$-C$_6$H$_3$—CH$_2$ |
| 278 | 2-CH$_2$CH$_3$—C$_6$H$_4$—CH$_2$ |
| 279 | 3-CH$_2$CH$_3$—C$_6$H$_4$—CH$_2$ |
| 280 | 4-CH$_2$CH$_3$—C$_6$H$_4$—CH$_2$ |
| 281 | 2-CH(CH$_3$)$_2$-C$_6$H$_4$—CH$_2$ |
| 282 | 3-CH(CH$_3$)$_2$-C$_6$H$_4$—CH$_2$ |
| 283 | 4-CH(CH$_3$)$_2$-C$_6$H$_4$—CH$_2$ |
| 284 | 3-C(CH$_3$)$_3$—C$_6$H$_4$—CH$_2$ |
| 285 | 4-C(CH$_3$)$_3$—C$_6$H$_4$—CH$_2$ |
| 286 | 2-C$_6$H$_5$—C$_6$H$_4$—CH$_2$ |
| 287 | 3-C$_6$H$_5$—C$_6$H$_4$—CH$_2$ |
| 288 | 4-C$_6$H$_5$—C$_6$H$_4$—CH$_2$ |
| 289 | 2-OCH$_3$—C$_6$H$_4$—CH$_2$ |
| 290 | 3-OCH$_3$—C$_6$H$_4$—CH$_2$ |
| 291 | 4-OCH$_3$—C$_6$H$_4$—CH$_2$ |
| 292 | 2,3-(OCH$_3$)$_2$—C$_6$H$_3$—CH$_2$ |
| 293 | 2,4-(OCH$_3$)$_2$—C$_6$H$_3$—CH$_2$ |
| 294 | 2,5-(OCH$_3$)$_2$—C$_6$H$_3$—CH$_2$ |
| 295 | 2,6-(OCH$_3$)$_2$—C$_6$H$_3$—CH$_2$ |
| 296 | 3,4-(OCH$_3$)$_2$—C$_6$H$_3$—CH$_2$ |
| 297 | 3,5-(OCH$_3$)$_2$—C$_6$H$_3$—CH$_2$ |
| 298 | 3,4,5-(OCH$_3$)$_3$—C$_6$H$_2$—CH$_2$ |
| 299 | 2-OCH$_2$CH$_3$—C$_6$H$_4$—CH$_2$ |
| 300 | 3-OCH$_2$CH$_3$—C$_6$H$_4$—CH$_2$ |
| 301 | 4-OCH$_2$CH$_3$—C$_6$H$_4$—CH$_2$ |
| 302 | 2-O(CH$_2$)$_2$CH$_3$—C$_6$H$_4$—CH$_2$ |
| 303 | 3-O(CH$_2$)$_2$CH$_3$—C$_6$H$_4$—CH$_2$ |
| 304 | 4-O(CH$_2$)$_2$CH$_3$—C$_6$H$_4$—CH$_2$ |
| 305 | 2-OCH(CH$_3$)$_2$—C$_6$H$_4$—CH$_2$ |
| 306 | 3-OCH(CH$_3$)$_2$—C$_6$H$_4$—CH$_2$ |
| 307 | 4-OCH(CH$_3$)$_2$—C$_6$H$_4$—CH$_2$ |
| 308 | 3-OC(CH$_3$)$_3$—C$_6$H$_4$—CH$_2$ |
| 309 | 4-OC(CH$_3$)$_3$—C$_6$H$_4$—CH$_2$ |
| 310 | 2-OCH$_2$CH=CH$_2$—C$_6$H$_4$—CH$_2$ |
| 311 | 3-OCH$_2$CH=CH$_2$—C$_6$H$_4$—CH$_2$ |
| 312 | 4-OCH$_2$CH=CH$_2$—C$_6$H$_4$—CH$_2$ |
| 313 | 2-CF$_3$—C$_6$H$_4$—CH$_2$ |
| 314 | 3-CF$_3$—C$_6$H$_4$—CH$_2$ |
| 315 | 4-CF$_3$—C$_6$H$_4$—CH$_2$ |
| 316 | 2-CO$_2$CH$_3$—C$_6$H$_4$—CH$_2$ |
| 317 | 2-SCH$_3$—C$_6$H$_4$—CH$_2$ |
| 318 | 3-SCH$_3$—C$_6$H$_4$—CH$_2$ |
| 319 | 4-SCH$_3$—C$_6$H$_4$—CH$_2$ |
| 320 | 2-OCF$_3$—C$_6$H$_4$—CH$_2$ |
| 321 | 3-OCF$_3$—C$_6$H$_4$—CH$_2$ |
| 322 | 4-OCF$_3$—C$_6$H$_4$—CH$_2$ |
| 323 | 2-OCHF$_2$—C$_6$H$_4$—CH$_2$ |
| 324 | 3-OCHF$_2$—C$_6$H$_4$—CH$_2$ |
| 325 | 4-OCHF$_2$—C$_6$H$_4$—CH$_2$ |
| 326 | 3-CF$_3$, 4-OCF$_3$—C$_6$H$_3$—CH$_2$ |
| 327 | 2-CH$_2$CH$_2$F—C$_6$H$_4$—CH$_2$ |
| 328 | 3-CH$_2$CH$_2$F—C$_6$H$_4$—CH$_2$ |
| 329 | 4-CH$_2$CH$_2$F—C$_6$H$_4$—CH$_2$ |
| 330 | 2-CH$_2$CF$_3$—C$_6$H$_4$—CH$_2$ |
| 331 | 3-CH$_2$CF$_3$—C$_6$H$_4$—CH$_2$ |
| 332 | CH$_2$C≡CH |
| 333 | CH$_2$C≡CCl |
| 334 | CH$_2$C≡CBr |
| 335 | CH$_2$C≡CI |
| 336 | CH$_2$C≡CCH$_3$ |
| 337 | CH$_2$C≡CCH$_2$CH$_3$ |

The compounds I are suitable for use as fungicides.

The compounds I are distinguished by an outstanding activity against a broad spectrum of phytopathogenic fungi, in particular from the class of the Ascomycetes, Phycomycetes and Basidiomycetes. Some of them act systemically and can be employed as foliar- and soil-acting fungicides in crop protection.

They are especially important for controlling a large number of fungi on a variety of crop plants such as wheat, rye, barley, oats, rice, maize, grass, cotton, soybeans, coffee, sugar cane, grapevines, fruit species, ornamentals and vegetables such as cucumbers, beans, and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, *Puccinia* species on cereals, *Rhizoctonia* species on cotton, rice and lawns, *Ustilago* species on cereals and sugar cane, *Venturia inaequalis* (scab) on apples, *Helminthosporium* species on cereals, *Septoria nodorum* on wheat, *Botrytis cinerea* (gray mold) on strawberries, vegetables, ornamentals and grapevines, *Cercospora arachidicola* on peanuts, *Pseudocercosporella herpotrichoides* on wheat, barley, *Pyricularia oryzae* on rice, *Phytophthora infestans* on potatoes and tomatoes, *Fusarium* and *Verticillium* species on a variety of plants, *Plasmopara viticola* on grapevines, *Alternaria* species on vegetables and fruit.

Moreover, the compounds I are suitable for controlling harmful fungi in the protection of materials (eg. wood, paper, fibers or tissues) and in the protection of stored products.

The compounds I are applied by treating the fungi, or the plants, seeds, materials or the soil to be protected against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the specific intended use; in any case, it should guarantee fine and uniform distribution of the compound according to the invention. The formulations are prepared in a known manner, eg. by extending the active ingredient with solvents and/or carriers, if desired using emulsifiers and dispersants, it also being possible to use other organic solvents as auxiliary solvents if water is used as the diluent. Suitable auxiliaries for this purpose are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates), and dispersants such as lignin-sulfite waste liquors and methylcellulose.

The fungicidal compositions generally comprise from 0.1 to 95, preferably from 0.5 to 90, % by weight of active ingredient.

Depending on the nature of the desired effect, the rates of application for use in crop protection are from 0.01 to 2.0 kg of active ingredient per ha.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the desired effect. Normal rates of application in the protection of materials are, for example, 0.001 g to 2 kg, preferably 0.005 g to 1 kg, of active ingredient per cubic meter of material treated.

In the use form as fungicides, the compositions according to the invention can also exist together with other active ingredients, e.g. with herbicides, insecticides, growth regulators, fungicides, or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-di-ethylphthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonyl-aminobenzimidazole, 2-(2-furyl) benzimidazole, 2-(4-thiazolyl)benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxylic acid cyclohexylamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-[1-(2,2,2-trichloroethyl)formamide], 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morphine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2, 6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1, 3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1, 2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2, 6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

The compounds of the formula I are furthermore suitable for effectively controlling pests from the class of the insects, arachnids and nematodes. They can be employed as pesticides in crop protection and in the hygiene, stored-product and veterinary sector.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, TipUla oleracea, TipUla paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monororium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, EUschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestics, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica*, cyst-forming nematodes, eg. *Globodera rostochiensis, Heterodera avenae, Heterodera glycines, Heterodera schachtii, Heterodera trifolii*, stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus*

*primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or the use forms prepared therefrom, for example in the form of ready-to-spray solutions, powders, suspensions or dispersions, emulsions, oil dispersions, pastes, dusts, materials for spreading or granules, by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can be varied within substantial ranges.

In general, they are from 0.0001 to 10%, preferably from 0.01 to 1%.

The active ingredients can also be used successfully in the ultra-low-volume method (ULV), it being possible to apply formulations with over 95% by weight of active ingredient, or even the active ingredient without additives.

Under field conditions, the rate of application of active ingredient for controlling pests is 0.1 to 2.0, preferably 0.2 to 1.0, kg/ha.

Substances which are suitable for the preparation of ready-to-spray solutions, emulsions, pastes or oil dispersions are mineral oil fractions of medium to high boiling point such as kerosene or diesel oil, furthermore coal-tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active ingredient, wetting agent, tackifier, dispersant or emulsifier and, if desired, solvent or oil, which are suitable for dilution with water.

Suitable surfactants are alkali metal, alkaline earth metal and ammonium salts of lignosulfonic acid, naphthalene-sulfonic acid, phenolsulfonic acid, dibutylnaphthalene-sulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powders, materials for spreading and dusts can be prepared by mixing or concomitantly grinding the active substances with a solid carrier.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

Examples of the formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a preparation of the active ingredient with good adhesion (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients onto solid carriers. Examples of solid carriers are mineral earths such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nut shell meal, cellulose powders, and other solid carriers.

Various types of oils, or herbicides, fungicides, other pesticides, or bactericides, can be added to the active ingredients, if appropriate also only just prior to use (tank mix). These agents can be admixed with the agents according to the invention in a weight ratio of 1:10 to 10:1.

SYNTHESIS EXAMPLES

The protocols given in the synthesis examples which follow were used for obtaining further compounds I by altering the starting compounds as required. The resulting compounds are listed in Table 1 below, with physical information

EXAMPLE 1 Preparation of [I-1]

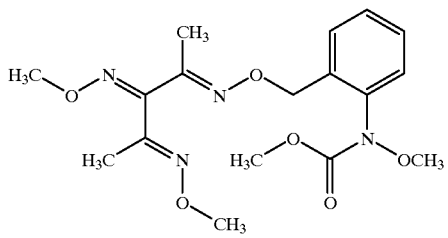

At 20–25° C., a solution of 0.95 g (0.005 mol) of 2,3,4-pentatrione 2-(E)-3-(Z)-bis(O-methyloxime) 4-(E)-oxime (cf.: DE-A 195 39 324), 2.0 g (0.006 mol) of methyl N-(2-bromomethylhenyl)-N-methoxycarbamate in 10 ml of dimethylformamide was stirred with 2.1 g (0.014 mol) of potassium carbonate for 20 hours. The reaction mixture was suspended in water and extracted with ethyl acetate. The combined organic phases were washed with sat. sodium chloride solution, dried and freed from the solvent. Silica gel chromatography (cyclohexane/ethyl acetate mixture 9:1) of the residue gave 1.4 g of the title compound as an oil.

$^1$H NMR (CDCl$_3$; δ in ppm): 1.8 (s, 3H); 2.08 (s, 3H); 3.70 (s, 3H); 3.77 (s, 3H); 3.90 (s, 3H); 3.95 (s, 3H); 5.20 (s, 2H); 7.20–7.50 (m, 4H).

TABLE I

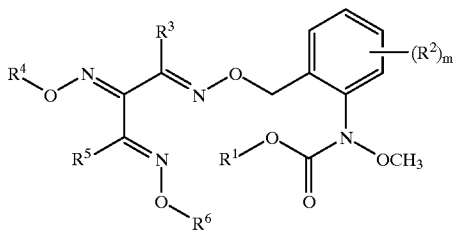

| No. | $R^2$ | $R^3$ | $R^4$ | $R^5$ | $R^6$ | Physical Data (IR [cm$^{-1}$], $^1$H NMR: δ [ppm]) |
|---|---|---|---|---|---|---|
| I-1 | H | CH$_3$ | CH$_3$ | CH$_3$ | CH$_3$ | IR: 1740, 1712, 1457, 1441, 1359, 1138, 1102, 1085, 1047, 895 |
| I-2 | H | CH$_3$ | C$_2$H$_5$ | CH$_3$ | CH$_3$ | $^1$H NMR (CDCl$_3$): 7,4(m, brd); 5.2(s); 4.2(q); 3.8; 3.7; 3.6(s); 2.1; 1.8(s); 1.2(t) |

TABLE I-continued

| No. | $R^2$ | $R^3$ | $R^4$ | $R^5$ | $R^6$ | Physical Data (IR [cm$^{-1}$], $^1$H NMR: δ [ppm]) |
|---|---|---|---|---|---|---|
| I-3 | H | CH$_3$ | C$_3$H$_3$ | CH$_3$ | CH$_3$ | IR: 1738, 1711, 1456, 1441, 1358, 1099, 1049, 1026, 1007, 892 |
| I-4 | H | CH$_3$ | CH$_3$ | CH$_3$ | C$_2$H$_5$ | IR: 1741, 1712, 1457, 1441, 1358, 1090, 1048, 1035, 872 |
| I-5 | H | CH$_3$ | CH$_3$ | CH$_3$ | CH(CH$_3$)$_2$ | IR: 1742, 1713, 1456, 1441, 1369, 1359, 1343, 1328, 1030, 956 |
| I-6 | H | CH$_3$ | CH$_3$ | CH$_3$ | C$_3$H$_3$ | IR: 1738, 1711, 1456, 1441, 1359, 1246, 1086, 1039, 1007, 884 |
| I-7 | H | CH$_3$ | C$_2$H$_5$ | CH$_3$ | C$_3$H$_3$ | IR: 1739, 1711, 1456, 1441, 1357, 1093, 1040, 1007, 978, 927 |
| I-8 | H | CH$_3$ | C$_3$H$_3$ | CH$_3$ | C$_3$H$_3$ | IR: 1736, 1710, 1456, 1441, 1357, 1093, 1041, 1028, 1005 |
| I-9 | H | CH$_3$ | CH$_3$ | CH$_3$ | C$_3$H$_5$ | IR: 1741, 1712, 1457, 1441, 1360, 1246, 1100, 1085, 1031, 886 |
| I-10 | H | CH$_3$ | C$_2$H$_5$ | CH$_3$ | C$_3$H$_5$ | IR: 1741, 1713, 1456, 1441, 1357, 1246, 1094, 1032, 998, 924 |
| I-11 | H | CH$_3$ | C$_3$H$_3$ | CH$_3$ | C$_3$H$_5$ | IR: 1739, 1711, 1456, 1441, 1358, 1245, 1103, 1027, 1007, 923 |

Examples of the Activity Against Harmful Fungi

The fungicidal activity of the compounds of the formula I was demonstrated by the following experiments:

The active ingredients were formulated, separately or together, as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

The compounds compiled in the table below, known from WO-A 97/15552, were used as comparative active ingredients:

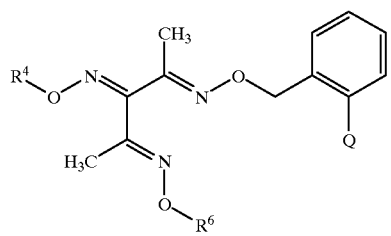

| Comparison No. | known from WO-A 97/15552 | Q | $R^4$ | $R^6$ |
|---|---|---|---|---|
| A.7 | Tab. 327, No. 919 | C(=NOCH$_3$)COOCH$_3$ | C$_2$H$_5$ | C$_3$H$_3$ |
| B.7 | Tab. 328, No. 919 | C(=NOCH$_3$)CONHCH$_3$ | C$_2$H$_5$ | C$_3$H$_3$ |
| C.7 | Tab. 325, No. 919 | C(=CHOCH$_3$)COOCH$_3$ | C$_2$H$_5$ | C$_3$H$_3$ |
| D.7 | Tab. 326, No. 919 | C(=CHCH$_3$)COOCH$_3$ | C$_2$H$_5$ | C$_3$H$_3$ |
| A.8 | Tab. 648, No. 919 | C(=NOCH$_3$)COOCH$_3$ | C$_3$H$_3$ | C$_3$H$_3$ |
| B.8 | Tab. 647, No. 919 | C(=NOCH$_3$)CONHCH$_3$ | C$_3$H$_3$ | C$_3$H$_3$ |
| C.8 | Tab. 645, No. 919 | C(=CHOCH$_3$)COOCH$_3$ | C$_3$H$_3$ | C$_3$H$_3$ |
| D.8 | Tab. 646, No. 919 | C(=CHCH$_3$)COOCH$_3$ | C$_3$H$_3$ | C$_3$H$_3$ |
| A.9 | Tab. 8, No. 827 | C(=NOCH$_3$)COOCH$_3$ | CH$_3$ | C$_3$H$_5$ |
| B.9 | Tab. 7, No. 827 | C(=NOCH$_3$)CONHCH$_3$ | CH$_3$ | C$_3$H$_5$ |
| C.9 | Tab. 5, No. 827 | C(=CHOCH$_3$)COOCH$_3$ | CH$_3$ | C$_3$H$_5$ |
| D.9 | Tab. 6, No. 827 | C(=CHCH$_3$)COOCH$_3$ | CH$_3$ | C$_3$H$_5$ |
| A.11 | Tab. 648, No. 827 | C(=NOCH$_3$)COOCH$_3$ | C$_3$H$_3$ | C$_3$H$_5$ |
| B.11 | Tab. 647, No. 827 | C(=NOCH$_3$)CONHCH$_3$ | C$_3$H$_3$ | C$_3$H$_5$ |
| C.11 | Tab. 645, No. 827 | C(=CHOCH$_3$)COOCH$_3$ | C$_3$H$_3$ | C$_3$H$_5$ |
| D.11 | Tab. 646, No. 827 | C(=CHCH$_3$)COOCH$_3$ | C$_3$H$_3$ | C$_3$H$_5$ |

Use Example 1—Curative Activity Against *Puccinia recondita* on Wheat (wheat leaf rust)

Leaves of potted weed seedlings of the variety "Frühgold" were dusted with spores of leaf rust (*Puccinia recondita*). Thereafter, the pots were kept for 24 hours in a chamber of high atmospheric humidity (90–95%), at 20–22° C. During this time, the spores germinated and the germinal tubes penetrated into the leaf tissue. The next day, the infected plants were sprayed to runoff point with an aqueous formulation of active ingredient prepared from a stock solution consisting of 10% of active ingredient, 63% of cyclohexanone and 27% of emulsifier. After the spray coating had dried on, the test plants were cultivated in a greenhouse at 20–22° C. and 65–70% relative atmospheric humidity for 7 days. Thereafter, the extent of rust fungus development on the leaves was determined.

In this test, the plants which had been treated with 16 ppm of the active ingredients I-7 and I-8 showed 0–25% infection, whereas the plants which had been treated with 16 ppm of the comparative active ingredients B.7, A.8, B.8, C.8 and D.8 were infected to 40–100% and the untreated plants were infected to 100%.

Use Example 2—Activity Against Net Blotch of Barley

Leaves of potted barley seedlings of the variety "Igri" were sprayed to runoff point with an aqueous preparation of active ingredient which had been prepared from a stock solution consisting of 10% of active ingredient, 63% of cyclohexanone and 27% of emulsifier. 24 hours after the spray coating had dried on, the leaves were inoculated with an aqueous spore suspension of Pyrenophora teres, the causative organism of net blotch. The test plants were subsequently placed in a greenhouse at 20–24° C. and 95–100% relative atmospheric humidity. After 6 days, the extent of the development of the disease was determined visually in % infection of the total leaf area.

In this test, the plants which had been treated with 63 ppm of the active ingredient I-7 showed 15% infection, whereas the plants which had been treated with 16 ppm of the comparative active ingredients A.7, B.7, C.7 and D.7 showed 25–100% infection, and the untreated plants showed 100% infection.

Use Example 3—Activity Against *Botrytis cinerea* on Bell Pepper Leaves

Bell pepper seedlings of the variety "Neusiedler Ideal Elite" were, after 4 to 5 leaves were well-developed, sprayed to runoff point with an aqueous preparation of active ingredient which had been prepared from a stock solution consisting of 10% of active ingredient, 63% of cyclohexanone and 27% of emulsifier. The next day, the treated plants were inoculated with a spore suspension of Botrytis cinerea containing $1.7 \times 10^6$ spores/ml in a 2% strength solution of Biomalz in water. The test plants were subsequently kept in a climatized chamber at 22–24° C. and high atmospheric humidity. After 5 days, the extent of the fungal infection on the leaves could be determined visually in %.

In this test, the plants which had been treated with 250 ppm of the active ingredient I-8, I-9 and I-11 showed 15–25% infection, whereas the plants which had been treated with 250 ppm of the comparative active ingredients A.8, B.8, C.8, D.8, A.9, B.9, D.9, A.11, B.11, C.11 and D.11 showed 40–100% infection, and the untreated plants showed 100% infection.

Examples of the Activity Against Animal Pests

The activity of the compounds of the general formula I against animal pests was demonstrated by the following experiments:

The active ingredients were formulated a. as a 0.1% strength solution in acetone or b. as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Wettol® EM (nonionic emulsifier based on ethoxylated castor oil) and diluted to give the desired concentration, using acetone in the case of a. and water in the case of b.

After the experiments had been concluded, in each case the lowest concentration was determined at which the compounds still caused an 80–100% inhibition or mortality in comparison with untreated control experiments (limit or minimal concentration).

Example 1 Activity Against *Nephotettix cincticeps* (Green rice leafhopper), Contact Action Filter disks (Ø 9 cm) were treated with 1 ml of the aqueous preparation of active ingredient and subsequently populated with five adult leafhoppers. The mortality was determined after 24 hours.

In this experiment, the active compound I-7 showed a limit concentration of 0.2 mg.

We claim:
1. A phenylcarbamate of the formula I

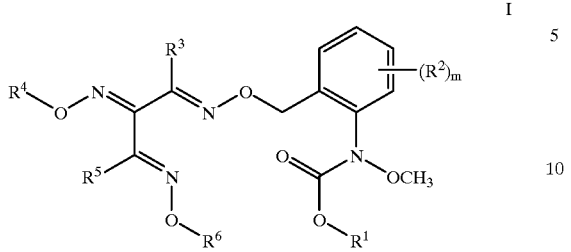

where:
R$^1$ is C$_1$–C$_4$-alkyl;
R$^2$ is cyano, nitro, trifluoromethyl, halogen, C$_1$–C$_4$-alkyl and C$_1$–C$_4$-alkoxy;
m is 0, 1 or 2, where the radicals R$^2$ may be different if m is 2;
R$^3$ is hydrogen, cyano, C$_1$–C$_4$-alkyl, C$_1$–C$_4$-haloalkyl, C$_3$–C$_6$-cycloalkyl;
R$^4$, R$^6$ independently of one another are each hydrogen,
C$_1$–C$_{10}$-alkyl, C$_3$–C$_6$-cycloalkyl, C$_2$–C$_{10}$-alkenyl, C$_2$–C$_{10}$-alkynyl, C$_1$–C$_{10}$-alkylcarbonyl, C$_2$–C$_{10}$-alkenylcarbonyl, C$_3$–C$_{10}$-alkynylcarbonyl or C$_1$–C$_{10}$-alkylsulfonyl, where these radicals may be partially or fully halogenated or may carry one to three of the following groups: cyano, nitro, hydroxyl, mercapto, amino, carboxyl, aminocarbonyl, aminothiocarbonyl, halogen, C$_1$–C$_6$-alkyl, C$_1$–C$_6$-haloalkyl, C$_1$–C$_6$-alkylsulfonyl, C$_1$–C$_6$-alkylsulfoxyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_2$–C$_6$-alkenyl, C$_2$–C$_6$-alkenyloxy, C$_3$–C$_6$-cycloalkyl, C$_3$–C$_6$-cycloalkyloxy, heterocyclyl, heterocyclyloxy, benzyl, benzyloxy, aryl, aryloxy, arylthio, hetaryl, hetaryloxy and hetarylthio, where the cyclic groups for their part may be partially or fully halogenated or may carry one to three of the following groups: cyano, nitro, hydroxyl, mercapto, amino, carboxyl, aminocarbonyl, aminothiocarbonyl, halogen, C$_1$–C$_6$-alkyl, C$_1$–C$_6$-haloalkyl, C$_1$–C$_6$-alkylsulfonyl, C$_1$–C$_6$-alkylsulfoxyl, C$_3$–C$_6$-cycloalkyl, C$_1$–C$_6$-alkoxy, C$_1$–C$_6$-haloalkoxy, C$_1$–C$_6$-alkyloxycarbonyl, C$_1$–C$_6$-alkylthio, C$_1$–C$_6$-alkylamino, di-C$_1$–C$_6$-alkylamino, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_2$–C$_6$-alkenyl, C$_2$–C$_6$-alkenyloxy, benzyl, benzyloxy, aryl, aryloxy, arylthio, hetaryl, hetaryloxy, hetarylthio or C(=NOR$^7$)—A$_n$—R$^8$;
aryl, arylcarbonyl, arylsulfonyl, hetaryl, hetarylcarbonyl or hetarylsulfonyl, where these radicals may be partially or fully halogenated or may carry one to three of the following groups: cyano, nitro, hydroxyl, mercapto, amino, carboxyl, aminocarbonyl, aminothiocarbonyl, halogen, C$_1$–C$_6$-alkyl, C$_1$–C$_6$-haloalkyl, C$_1$–C$_6$-alkylcarbonyl, C$_1$–C$_6$-alkylsulfonyl, C$_1$–C$_6$-alkylsulfoxyl, C$_3$–C$_6$-cycloalkyl, C$_1$–C$_6$-alkoxy, C$_1$–C$_6$-haloalkoxy, C$_1$–C$_6$-alkyloxycarbonyl, C$_1$–C$_6$-alkylthio, C$_1$–C$_6$-alkylamino, di-C$_1$–C$_6$-alkylamino, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_2$–C$_6$-alkenyl, C$_2$–C$_6$-alkenyloxy, benzyl, benzyloxy, aryl, aryloxy, hetaryl, hetaryloxy or C(=NOR$^7$)—A$_n$—R$^8$;
R$^5$ is hydrogen,
C$_1$–C$_6$-alkyl, C$_2$–C$_6$-alkenyl, C$_2$–C$_6$-alkynyl, where the hydrocarbon radicals of these groups may be partially or fully halogenated or may carry one to three of the following radicals: cyano, nitro, hydroxyl, mercapto, amino, carboxyl, aminocarbonyl, aminothiocarbonyl, halogen, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_1$–C$_6$-alkylsulfonyl, C$_1$–C$_6$-alkylsulfoxyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_2$–C$_6$-alkenyloxy, C$_3$–C$_6$-cycloalkyl, C$_3$–C$_6$-cycloalkyloxy, heterocyclyl, heterocyclyloxy, aryl, aryloxy, aryl-C$_1$–C$_4$-alkoxy, arylthio, aryl-C$_1$–C$_4$-alkylthio, hetaryl, hetaryloxy, hetaryl-C$_1$–C$_4$-alkoxy, hetarylthio, hetaryl-C$_1$–C$_4$-alkylthio, where the cyclic radicals for their part may be partially or fully halogenated and/or may carry one to three of the following groups: cyano, nitro, hydroxyl, mercapto, amino, carboxyl, aminocarbonyl, aminothiocarbonyl, C$_1$–C$_6$-alkyl, C$_1$–C$_6$-haloalkyl, C$_1$–C$_6$-alkylsulfonyl, C$_1$–C$_6$-alkylsulfoxyl, C$_3$–C$_6$-cycloalkyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_2$–C$_6$-alkenyl, C$_2$–C$_6$-alkenyloxy, benzyl, benzyloxy, aryl, aryloxy, arylthio, hetaryl, hetaryloxy, hetarylthio and C(=NOR$^7$)—A$_n$—R$^8$;
C$_3$–C$_6$-cycloalkyl, C$_3$–C$_6$-cycloalkenyl, heterocyclyl, aryl, hetaryl, where the cyclic radicals may be partially or fully halogenated or may carry one to three of the following groups: cyano, nitro, hydroxyl, mercapto, amino, carboxyl, aminocarbonyl, aminothiocarbonyl, halogen, C$_1$–C$_6$-alkyl, C$_1$–C$_6$-haloalkyl, C$_1$–C$_6$-alkylsulfonyl, C$_1$–C$_6$-alkylsulfoxyl, C$_3$–C$_6$-cycloalkyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_2$–C$_6$-alkenyl, C$_2$–C$_6$-alkenyloxy, benzyl, benzyloxy, aryl, aryloxy, hetaryl and hetaryloxy;
where
A is oxygen, sulfur or nitrogen and where the nitrogen carries hydrogen or C$_1$–C$_6$-alkyl;
n is 0 or 1;

$R^7$ is hydrogen or $C_1$–$C_6$-alkyl and
$R^8$ is hydrogen or $C_1$–$C_6$-alkyl,
and salts thereof.

2. A compound of the formula I as claimed in claim 1 in which m is 0.

3. A compound of the formula I as claimed in claim 1 in which $R^1$ is methyl.

4. A compound of the formula I as claimed in claim 1 in which $R^3$ is hydrogen, cyano, cyclopropyl, methyl, ethyl or 1-methylethyl.

5. A compound of the formula I as claimed in claim 1 in which $R^4$ is hydrogen, $C_1$–$C_6$-alkyl, $C_2$–$C_6$-alkenyl, $C_2$–$C_6$-alkynyl, allyl, arylalkyl, hetarylalkyl, aryloxyalkyl, hetaryloxyalkyl, aryl or hetaryl.

6. A compound of the formula I as claimed in claim 1 in which $R^5$ is hydrogen, cyclopropyl, methyl, ethyl, isopropyl, unsubstituted or substituted aryl or hetaryl.

7. A compound of the formula I as claimed in claim 1 in which $R^6$ is $C_1$–$C_6$-alkyl, $C_2$–$C_6$-alkenyl, $C_2$–$C_6$-alkynyl, arylalkyl, hetarylalkyl, aryloxyalkyl or hetaryloxyalkyl.

8. A process for preparing compounds of the formula I, which comprises reacting a benzyl derivative of the formula II with a hydroxyimine of the formula III,

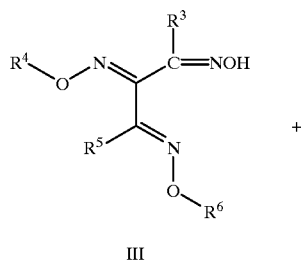

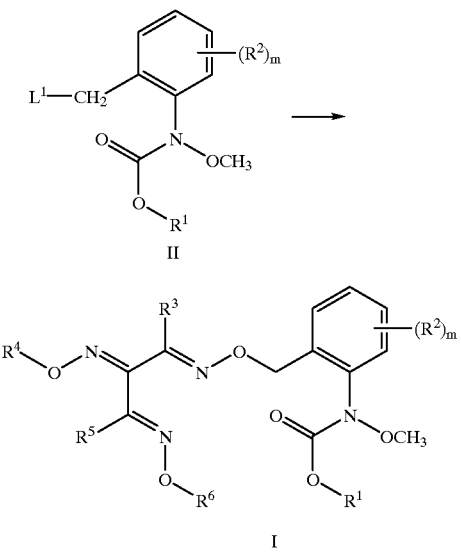

in which $L^1$ is a nucleophilically replaceable leaving group.

9. A composition against animal pests or harmful fungi, comprising customary additives and an effective amount of a compound of the formula I as claimed in claim 1.

10. A composition as claimed in claim 9 for controlling animal pests from the class of the insects, arachnids or nematodes.

* * * * *

UNITED STATES PATENT AND TRADEMARK OFFICE
CERTIFICATE OF CORRECTION

PATENT NO.   : 6,232,339 B1
DATED        : May 15, 2001
INVENTOR(S)  : Gypser et al.

Page 1 of 1

It is certified that error appears in the above-identified patent and that said Letters Patent is hereby corrected as shown below:

Column 30, claim 1,
Line 10, "$C(=NOR^7)-A_n-R_8$" should be -- $C(=NOR^7)-A_n-R^8$ --.

Signed and Sealed this

Twenty-seventh Day of November, 2001

Attest:

NICHOLAS P. GODICI
Attesting Officer
Acting Director of the United States Patent and Trademark Office